(12) United States Patent
Kim et al.

(10) Patent No.: US 9,034,265 B2
(45) Date of Patent: May 19, 2015

(54) BIOMOLECULAR SENSOR WITH PLURAL METAL PLATES AND MANUFACTURING METHOD THEREOF

(75) Inventors: Yong Hyup Kim, Seoul (KR); Young June Park, Seoul (KR); Jung Woo Ko, Seoul (KR); Tae June Kang, Seoul (KR); Seok Hyang Kim, Seoul (KR); Jae Heung Lim, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 1185 days.

(21) Appl. No.: 13/062,275

(22) PCT Filed: May 22, 2009

(86) PCT No.: PCT/KR2009/002728
§ 371 (c)(1),
(2), (4) Date: May 31, 2011

(87) PCT Pub. No.: WO2009/151219
PCT Pub. Date: Dec. 17, 2009

(65) Prior Publication Data
US 2011/0223065 A1   Sep. 15, 2011

(30) Foreign Application Priority Data
Jun. 11, 2008   (KR) .................. 10-2008-0054438

(51) Int. Cl.
| | | |
|---|---|---|
| *G01N 27/06* | (2006.01) | |
| *B82Y 15/00* | (2011.01) | |
| *G01N 27/414* | (2006.01) | |

(52) U.S. Cl.
CPC ............ *B82Y 15/00* (2013.01); *G01N 27/4145* (2013.01); *G01N 27/4146* (2013.01); *Y10S 977/957* (2013.01)

(58) Field of Classification Search
CPC ................................ G01N 27/06; B82Y 15/00
See application file for complete search history.

(56) References Cited

U.S. PATENT DOCUMENTS

| 6,528,020 B1 | 3/2003 | Dai et al. |
| 6,689,674 B2 * | 2/2004 | Zhang et al. .................. 438/584 |
| 2008/0094078 A1 | 4/2008 | So et al. |

FOREIGN PATENT DOCUMENTS

KR   10-2003-0085272   11/2003
(Continued)

OTHER PUBLICATIONS (C.-Z. Li et al., Impedance Sensing of DNA Binding Drugs Using Gold Substrates Modified with Gold Nanoparticles, 77 Anal. Chem. 478-485 (2005)).*
K. A. Mahmoud, Picomolar Detection of Protease Using Peptide/Single Walled Carbon Nanotube/Gold Nanoparticle-Modified Electrode, 2 ACS NANO 1051-1057 (2008).*
Korean Intellectual Property Office, International Search Report for International Application No. PCT/KR2009/002728, Sep. 14, 2009.

(Continued)

*Primary Examiner* — Randy Boyer
(74) *Attorney, Agent, or Firm* — Sherr & Jiang, PLLC

(57) ABSTRACT

Disclosed are a biomolecular sensor and a method of fabricating the same having high sensitivity and resolution by using a plurality of metal plates that change electrical properties of a plurality of nanostructures according to the attachment of biomolecules. The biomolecular sensor includes a substrate, first and second electrodes disposed to be spaced apart from each other on the substrate, a plurality of nanostructures disposed on the substrate to connect the first and second electrodes to each other, and a plurality of metal plates that change electrical properties of the plurality of nanostructures according to the attachment of biomolecules.

12 Claims, 10 Drawing Sheets

(56) References Cited

FOREIGN PATENT DOCUMENTS

| KR | 10-2004-0107225 | 12/2004 |
| KR | 10-2007-0000667 | 1/2007 |
| KR | 10-2007-0002111 | 1/2007 |

OTHER PUBLICATIONS

Korean Intellectual Property Office, Written Opinion of the International Searching Authority for International Application No. PCT/KR2009/002728, Sep. 14, 2009.

* cited by examiner

FIG.3
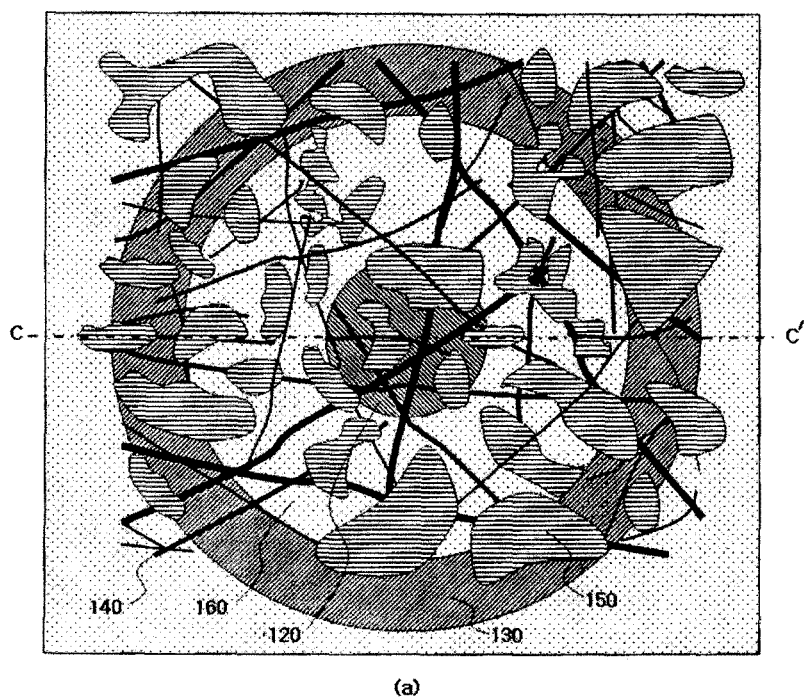
(a)
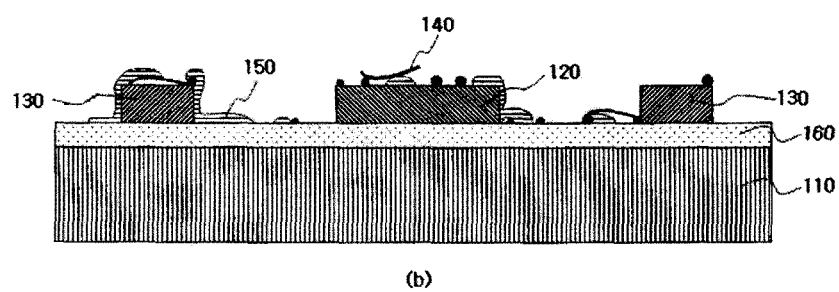
(b)

FIG.6
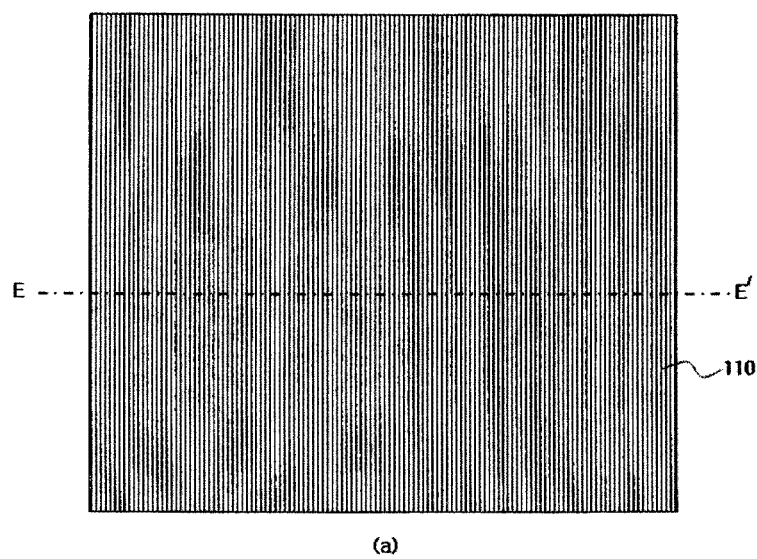
(a)
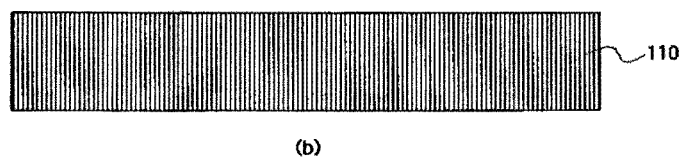
(b)

FIG.7
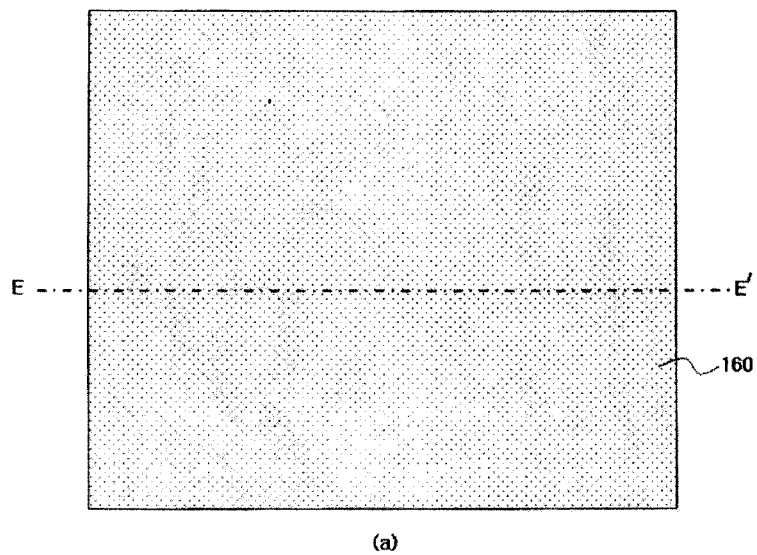
(a)
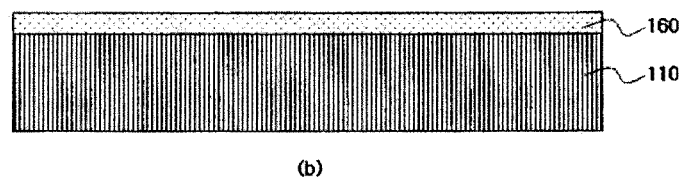
(b)

BIOMOLECULAR SENSOR WITH PLURAL METAL PLATES AND MANUFACTURING METHOD THEREOF

CROSS REFERENCE TO PRIOR APPLICATIONS

This application is a National Stage Patent Application of PCT International Patent Application No. PCT/KR2009/002728 (filed on May 22, 2009) under 35 U.S.C. §371, which claims priority to Korean Patent Application No. 10-2008-0054438 (filed on Jun. 11, 2008), which are all hereby incorporated by reference in their entirety.

TECHNICAL FIELD

The present invention relates to a biomolecular sensor having a plurality of metal plates and a method of fabricating the same.

BACKGROUND ART

Recently, interest in chemical and biological sensors using nanostructures (e.g., carbon nanotubes) sensitive to ambient environment has increased, and various types of sensors based on the nanostructures have been proposed.

A conventional nanostructure sensor has been disclosed in "B. L. Allen, P. D. Kichambare, A. Star, "Carbon Nanotube Field-Effect-Transistor-Based Biosensors," Adv. Mater. Vol. 19, pp. 1439-1451, 2007." The paper discloses a technique of sensing a specific DNA by attaching a thiolated single-stranded DNA (hereinafter, referred to as an ssDNA) to a nanostructure sensor and measuring a change in electric conductivity generated when hybridizing a complementary ssDNA using the ssDNA as a probe. The DNA sensing technique proposed in the prior literature is a method of sensing a change in electric conductivity based on the hybridization between the probe ssDNA and the complementary ssDNA, performed on an electrode (e.g., gold (Au)).

DISCLOSURE

Technical Problem

An aspect of the present invention is to provide a biomolecular sensor having a new structure different from a conventional sensor and a method of fabricating the same.

Another aspect of the present invention is to provide a biomolecular sensor having improved detection sensitivity and a method of fabricating the same.

Still another aspect of the present invention is to provide a biomolecular sensor capable of being easily produced and a method of fabricating the same.

Technical Solution

In accordance with a first aspect of the present invention, there is provided a biomolecular sensor including: a substrate; first and second electrodes disposed to be spaced apart from each other on the substrate; a plurality of nanostructures disposed on the substrate and configured to connect the first and second electrodes to each other; and a plurality of metal plates configured to change electrical properties of the plurality of nanostructures according to the attachment of biomolecules.

In accordance with a second aspect of the present invention, there is provided a method of fabricating a biomolecular sensor, including the steps of: (a) preparing a substrate; (b) forming first and second electrodes spaced apart from each other on the substrate; (c) forming a plurality of nanostructures that connect the first and second electrodes to each other; and (d) forming a plurality of metal plates on a top or bottom side of the plurality of nano structures, wherein step (d) is performed before or after step (c).

Advantageous Effects

A biomolecular sensor and a method of fabricating the same according to the present invention can improve the sensitivity of the biomolecular sensor.

Also, the biomolecular sensor and the method of fabricating the same according to the present invention using a physical vapor deposition process does not change physical properties of nanostructures, so that unique properties of the nanostructures are preserved.

Also, the biomolecular sensor and the method of fabricating the same according to the present invention using the physical vapor deposition process can easily adjust the size of metal particles. Further, a series of processes can be performed by using a semiconductor process, and thus productivity can be improved.

DESCRIPTION OF DRAWINGS

FIG. 3 is a drawing illustrating a second modification in which the arrangement of the electrodes 120 and 130 shown in FIG. 1 are changed.

FIGS. 6 to 10 illustrate processes in a method of fabricating the biomolecular sensor according to the first embodiment of the present invention.

MODE FOR INVENTION

Figure 1:
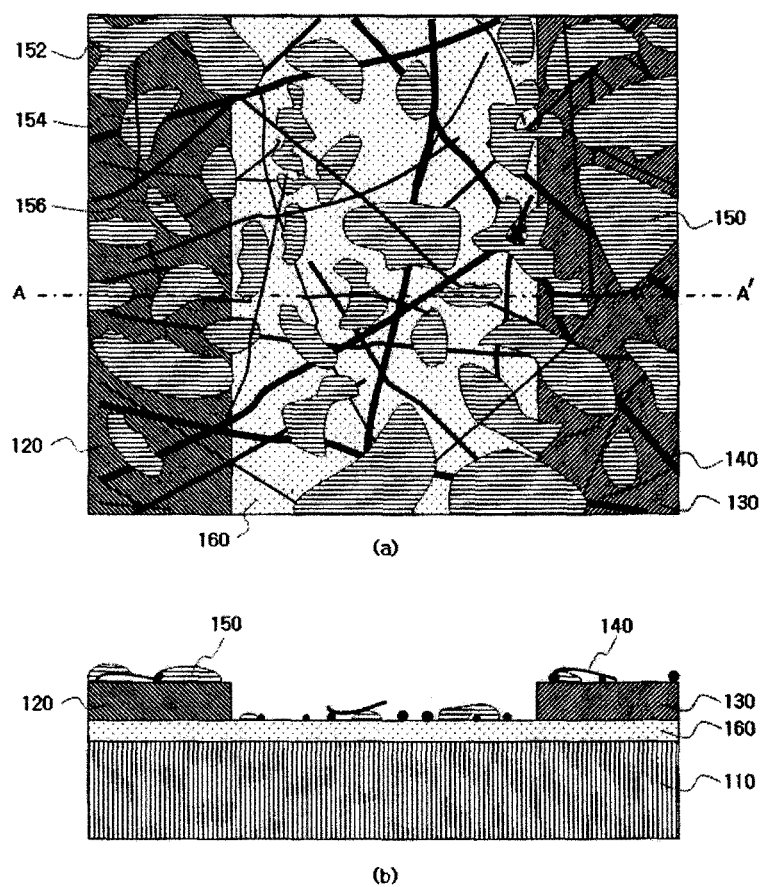
FIG. 1 is a view showing a biomolecular sensor according to a first embodiment of the present invention.

The present invention now will be described more fully hereinafter with reference to the accompanying drawings, in which embodiments of the invention are shown. This invention should not be construed as limited to the embodiments set forth herein. Rather, these embodiments are provided so that this disclosure will be thorough and complete, and will fully convey the scope of the invention to those skilled in the art. In the drawings, the widths, lengths or thicknesses of elements are exaggerated for clarity. Like numbers refer to like elements throughout.

It will be understood that when an element is referred to as being "on" another element, it can be directly on the other element or intervening elements may also be present. In contrast, when an element is referred to as being, for example, "directly on" another element, there are no intervening elements present. It will also be appreciated by those of skill in the art that references to a structure or feature that is disposed "adjacent" another feature may have portions that overlap or underlie the adjacent feature.

FIG. 1 is a view showing a biomolecular sensor according to a first embodiment of the present invention. (a) and (b) of FIG. 1 show plan and sectional views of the biomolecular sensor, respectively.

Referring to FIG. 1, the biomolecular sensor includes a substrate 110, a first electrode 120, a second electrode 130, a plurality of nanostructures 140 and a plurality of metal plates 150. The biomolecular sensor may further include an insulating layer 160. The biomolecular sensor may further include at least one additional first electrode (not shown), at least one additional second electrode (not shown) and a plurality of additional nanostructures (not shown).

The substrate 110 may be, for example, a semiconductor substrate, a conductive substrate, a non-conductive substrate, or a silicon on insulator (SOI) substrate. The semiconductor substrate may be, for example, a silicon substrate or a Group III-V semiconductor substrate. The conductive substrate may be, for example, a metal substrate or a conductive organic compound substrate. The non-conductive substrate may be, for example, a glass substrate or a polymer compound substrate. The examples are illustratively provided, and various other substrates may be used.

The first and second electrodes 120 and 130 are disposed to be spaced apart from each other on the substrate 110. The first and second electrodes 120 and 130 may be, for example, metal or doped poly silicon. The first and second electrodes 120 and 130 may include, for example, gold (Au). Although the first and second electrodes 120 and 130 have a rectangular shape in the first embodiment, the first and second electrodes 120 and 130 may have various other shapes such as an elliptical shape, a circular shape, a polygonal shape and a combination thereof, as long as the first and second electrodes 120 and 130 are electrically insulated from each other.

The plurality of nanostructures 140 are disposed on the substrate 110 and connected to the first and second electrodes 120 and 130. The connection of the plurality of nanostructures 140 to the first and second electrodes 120 and 130 is not limited to those of the plurality of nanostructures 140 to the respective first and second electrodes 120 and 130. More specifically, a portion of one of the plurality of nanostructures 140 is electrically connected to the first electrode 120, and a portion of another of the plurality of nanostructures 140 is electrically connected to the second electrode 130. The one nanostructure and the other nanostructure may be electrically connected to each other. Alternatively, a portion of one of the plurality of nanostructures 140 is electrically connected to the first electrode 120, and a portion of another of the plurality of nanostructures 140 is electrically connected to the second electrode 130. The one nanostructure and the other nanostructure may be electrically connected to each other through still another of the plurality of nanostructures 140. As an embodiment, the nanostructures may be densely positioned like an entangled mesh.

Various kinds of nanostructures may be used as the plurality of nanostructures 140. For example, nanotubes, nanowires, nanorods, nanoribbons, nanofilms or nanoballs may be used as the plurality of nanostructures 140. In addition, carbon nanotubes (hereinafter, briefly referred to as CNTs), semiconductor nanowires or conductive polymers may be used as the plurality of nanostructures 140. The CNTs may be classified into CNTs having properties of metal and CNTs having properties of a semiconductor according to their electrical properties. The CNTs may also be classified into single-walled CNTs, double-walled CNTs and multi-walled CNTs according to the number of walls. The material constituting the semiconductor nanowire may include at least one of various materials including $SnO_2$, $ZnO$, $In_2O_3$, $CdO$ and the like. The examples are illustratively provided, and various other materials may be used.

As an embodiment, each of the plurality of nanostructures 140 may have a length much greater than dimensions of its section. The plurality of nanostructures 140 may include wires, ribbon and tubes. As an embodiment, the plurality of nanostructures 140 may be disposed on a structure on which the plurality of nanostructures 140 are positioned so as to be stretched in parallel to a surface of the structure.

The plurality of metal plates 150 change electrical properties of the plurality of nanostructures 140 according to the attachment of biomolecules (not shown). The plurality of metal plates 150 may be disposed through a physical vapor deposition process without an annealing process, or may be disposed through the physical vapor deposition process and the annealing process. When the physical vapor deposition process and the annealing process are applied, contact characteristics may be improved between the plurality of nanostructures 140 and the electrodes 120 and 130. The plurality of metal plates 150 have a planar structure in which an area of a top surface of the plurality of metal plates has a size of greater than that of a square of a thickness of the plurality of metal plates 150 (e.g., the size of the area is four times greater than that of a square of the thickness). The area of the top surface of the plurality of metal plates 150 means a horizontal area when the plurality of metal layers 150 are viewed from the top thereof. The thickness of the plurality of metal plates 150 means a maximum height thereof. The top and bottom surfaces of the metal plate 150 may be parallel to each other, and may have various curvatures according to shapes of the nanostructure 140 positioned below the metal plate 150. The biomolecules may be, for example, proteins, deoxyribonucleic acids (hereinafter, briefly referred to as DNAs), molecules, ions or the like. Functionalization that allows the plurality of metal plates 150 to react with a specific biomolecule may be performed, so that the plurality of metal plates 150 have selectivity among various biomolecules, i.e., so that the electrical properties of the plurality of nanostructures 140 adjacent to the plurality of the metal plates 150 are changed depending on a specific biomolecule of the various biomolecules.

As an embodiment, the functionalization influences the plurality of metal plates 150 to detect proteins, tumor markers, molecules and viruses, so that the biomolecular sensor can detect electrical characteristics. The plurality of metal plates 150 may be exposed e to the biomolecules of a liquid or gaseous phase. The biomolecules may be included in liquid or gas.

As an embodiment, at least one of the plurality of metal plates 150 may be disposed between one and another of the plurality of nanostructures 140 according to the arrangement density of the plurality of nanostructures 140. An example in which a metal plate 152 is positioned on the plurality of nanostructures 140 is shown in this figure. Also, an example in which a metal plate 154 is positioned between the plurality of nanostructures 140 is shown in this figure. Also, an example in which a metal plate 156 is positioned in a space between the plurality of nanostructures 140 is shown in this figure.

The insulating layer 160 electrically isolates the first electrode 120, the second electrode 130, the plurality of nanostructures 140 and the plurality of metal plates 150 from the substrate 110. The insulating layer 160 may include an oxide layer such as $SiO_2$, $Al_2O_3$, $Ta_2O_5$, $ZrO_2$, $HfO_2$ or $TiO_2$, a nitride layer such as $SiON$ or $Si_3N_4$, and an Hf-based insulating layer such as HfsiON or HfSiOx. The examples are illustratively provided and various other materials having insulation properties may be used. Where a non-conductive substrate is used as the substrate 110, the insulating layer 160 may be omitted.

The biomolecular sensor may be implemented in the form of an array including a plurality of first and second electrodes. More specifically, the biomolecular sensor may further include at least one additional first electrode (not shown), at least one additional second electrode (not shown) and a plurality of additional nanostructures (not shown). The at least one additional first electrode (not shown) is disposed to be spaced apart from the first and second electrodes 120 and 130 on the substrate 110. Each of the at least one additional first electrode (not shown) has a second electrode corresponding to the additional first electrode among the at least one additional second electrode. The at least one additional second electrode (not shown) is disposed to be spaced apart from the first electrode 120, the second electrode 130 and the at least one additional first electrode (not shown) on the substrate 110. At least one of the plurality of additional nanostructures (not shown) is connected to a first electrode corresponding to the at least one additional nanostructure among the at least additional first electrode (not shown) and a second electrode corresponding to the at least one additional nanostructure among the at least additional second electrode (not shown).

Figure 2:
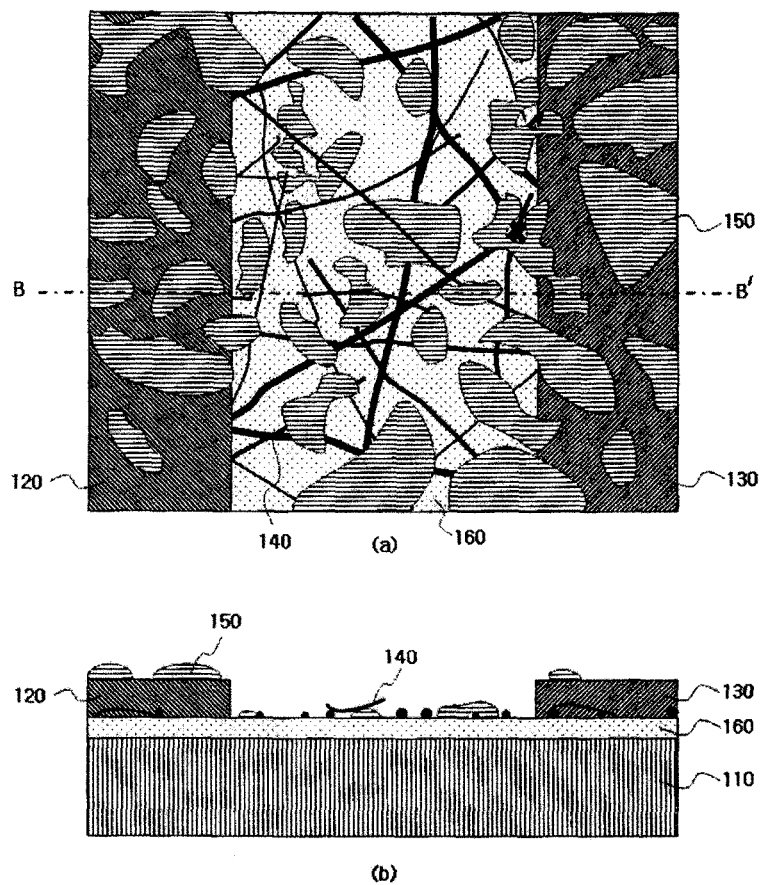
FIG. 2 is a view illustrating a first modification in which relative positions of a plurality of nanostructures 140 and electrodes 120 and 130, which are shown in FIG.1, are changed.

FIG. 2 is a view illustrating a first modification of the first embodiment in which the relative positions of the plurality of nanostructures 140 and the electrodes 120 and 130 in FIG. 1 are changed. (a) and (b) of FIG. 2 show plan and sectional views of the biomolecular sensor, respectively. The sectional view in the figure is a sectional view taken along line B-B' of the plan view.

Referring to FIG. 2, the first and second electrodes 120 and 130 are disposed on the plurality of nanostructures 140. When the plurality of nanostructures 140 are positioned below the first and second electrodes 120 and 130, contact characteristics between the plurality of nanostructures 140 and the first and second electrodes 120 and 130 are improved, thereby reducing contact resistance. In the first modification, the structures and materials of the substrate 110, the first electrode 120, the second electrode 130, the plurality of nanostructures 140, the plurality of metal plates 150 and the insulating layer 160 are substantially identical or similar to those in the first embodiment of the present invention, and thus, their descriptions will be omitted for convenience of illustration.

FIG. 3 is a view illustrating a second modification of the first embodiment in which the arrangement of the electrodes 120 and 130 in FIG. 1 are changed. (a) and (b) of FIG. 3 show plan and sectional views of the biomolecular sensor, respectively. The sectional view in the figure is a sectional view taken along line C-C' of the plan view.

Referring to FIG. 3, the first electrode 120 is disposed in the inside of the second electrode 130. The second electrode 130 surrounds the first electrode 120. A reference voltage that is a predetermined voltage may be applied to the second electrode 130. The biomolecular sensor may interact with a carrier for biomolecules. As an embodiment, the carrier may be a liquid such as water, or gas. Where the biomolecules are included in a predetermined liquid as the carrier, the resistance of the plurality of nanostructures 140 may be changed depending on the potential of the liquid adjacent to the plurality of nanostructures 140. Here, the potential of the liquid adjacent to the plurality of nanostructures 140 is variable, and thus, the measurement accuracy of the biomolecular sensor may be degraded. Accordingly, the reference voltage is applied to the second electrode 130, so that the potential of the liquid adjacent to the plurality of nanostructures 140 can be maintained more constant, thereby improving the measurement accuracy of the biomolecular sensor. The reference voltage may be, for example, a power voltage or ground voltage. As another embodiment, the carrier may be positioned in a gaseous or liquid state in the gas or liquid. As still another embodiment, the carrier may be a solution itself, or may be positioned in the solution. The examples are illustratively provided for, and various other types of carriers may be used.

The biomolecular sensor may not require a patterning process of the plurality of the nanostructures 140. In the conventional technology, the patterning process of the plurality of the nanostructures 140 is used to prevent the plurality of nanostructures 140 from being connected not only to first and second electrodes but also to a neighboring first electrode (not shown). in an embodiment, instead of the patterning process of the plurality of the nanostructures 140, the reference voltage is applied to the second electrode 130. In the conventional biomolecular sensor using a plurality of nanostructures, the plurality of nanostructures may be connected between a first electrode and a neighboring first electrode due to a processing error or the like. In this case, an exact measurement may not be performed due to interference of the plurality of nanostructures between the first electrode and the neighboring first electrode. However, in the biomolecular sensor according to an embodiment of the present invention, although a plurality of nanostructures are connected between the first electrode and the neighboring first electrode, the plurality of nanostructures are connected to a second electrode (to which the reference voltage is applied) positioned between the first electrode and the neighboring first electrode. Thus, interference does not occur between the first electrode and the neighboring first electrode. Accordingly, the sensor according to an embodiment of the present invention is robust against the processing error or the like.

The biomolecular sensor has a plurality of metal plates 150, and the plurality of metal plates 150 are disposed through a physical vapor deposition and an annealing process. The physical vapor deposition process and the annealing process can improve contact characteristics between the plurality of nanostructures 140 and the electrodes 120 and 130 through the physical vapor deposition process and the annealing process.

Although it has been illustrated in the second modification that the plurality of nanostructures 140 are disposed on the electrodes 120 and 130, the plurality of nanostructures 140 may be positioned below the electrodes 120 and 130 so as to improve contacts between the plurality of nanostructures 140 and the electrodes 120 and 130, as described in the first modification shown in FIG. 2. Although it has been illustrated in the second modification that the electrodes 120 and 130 are formed in the shape of a circle, the electrodes 120 and 130 may have various other shapes such as an elliptical shape, a circular shape, a polygonal shape and a combination thereof, as long as the electrodes 120 and 130 are electrically insulated from each other. In the second modification, the structures and materials of the substrate 110, the first electrode 120, the second electrode 130, the plurality of nanostructures 140, the plurality of metal plates 150 and the insulating layer 160 are substantially identical or similar to those in the first embodiment of the present invention, and thus, their descriptions will be omitted for convenience of illustration.

Figure 4:
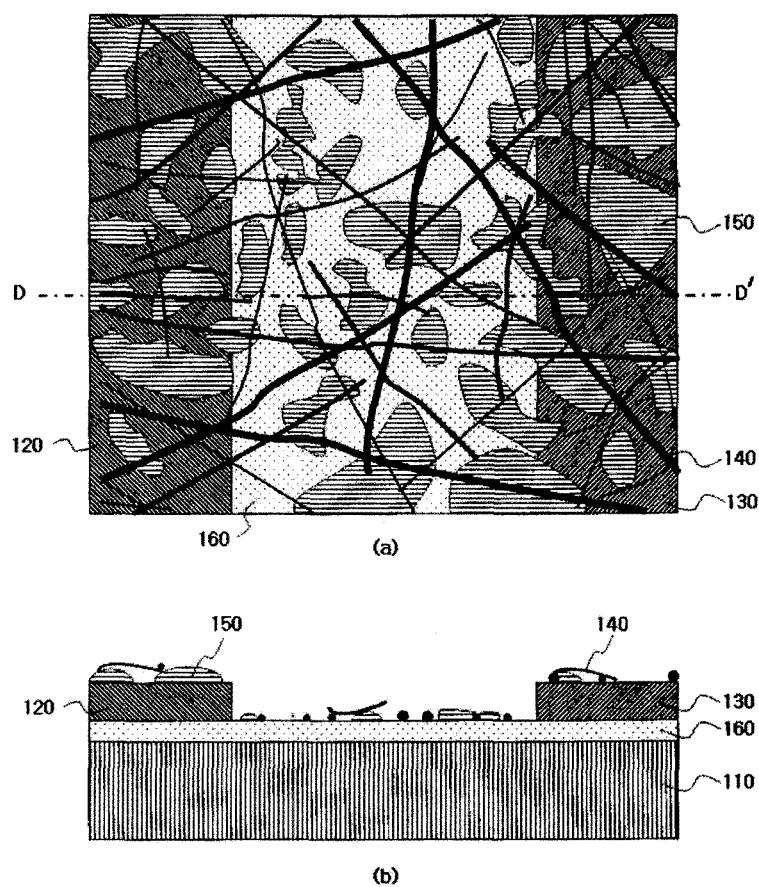
FIG. 4 is a view showing a biomolecular sensor according to a second embodiment of the present invention.

FIG. 4 is a view showing a biomolecular sensor according to a second embodiment of the present invention. (a) and (b) of FIG. 4 show plan and sectional views of the biomolecular sensor, respectively. The sectional view in this figure is a sectional view taken along line D-D' of the plan view.

Referring to FIG. 4, the biomolecular sensor includes a substrate 110, a first electrode 120, a second electrode 130, a plurality of nanostructures 140 and a plurality of metal plates 150. The biomolecular sensor may further include an insulating layer 160.

In the biomolecular sensor according to the first embodiment of the present invention, the plurality of metal plates 150 are disposed after the plurality of nanostructures 140 are disposed. However, in the biomolecular sensor according to the second embodiment of the present invention, the plurality of nanostructures 140 are disposed after the plurality of metal plates 150 are disposed. An example in which the metal plates 150 are positioned below the plurality of nanostructures 140 are shown in this figure. In the second embodiment, the structures and materials of the substrate 110, the first electrode 120, the second electrode 130, the plurality of nanostructures 140 and the plurality of metal plates 150 are substantially identical or similar to those in the first embodiment of the present invention, and thus, their descriptions will be omitted for convenience of illustration.

A biomolecular sensor according to a third embodiment of the present invention includes a substrate 110, a first electrode 120, a second electrode 130, a plurality of nanostructures 140 and a plurality of metal plates 150. The biomolecular sensor may further include an insulating layer 160.

In the biomolecular sensor according to the first embodiment of the present invention, the plurality of metal plates 150 are disposed after the plurality of nanostructures 140 are disposed. In the biomolecular sensor according to the second embodiment of the present invention, the plurality of nanostructures 140 are disposed after the plurality of metal plates 150 are disposed. However, in the biomolecular sensor according to the third embodiment of the present invention, the plurality of metal plates 150 are disposed after a plurality of first nanostructures (corresponding to the plurality of nanostructures 140) are disposed. Then, a plurality of second nanostructures (not shown) are additionally disposed after the disposition of the plurality of metal plates 150. The plurality of the second nanostructures (not shown) are disposed on the substrate 110 in the same manner as the first nanostructures 140, and have a similar shape to the plurality of first nanostructures 140. The plurality of metal plates 150 according to the third embodiment of the present invention are disposed between the first nanostructures 140 and the second nanostructures (not shown).

As an embodiment, at least one of the plurality of metal plates 150 may be disposed below any one of the plurality of first nanostructures 140 according to the arrangement density of the plurality of first nanostructures 140. In the third embodiment, the structures and materials of the substrate 110, the first electrode 120, the second electrode 130, the plurality of first nanostructures 140, the plurality of second nanostructures (not shown) and the plurality of metal plates 150 are substantially identical or similar to those in the first embodiment of the present invention, and thus, their descriptions will be omitted for convenience of illustration.

Figure 5:
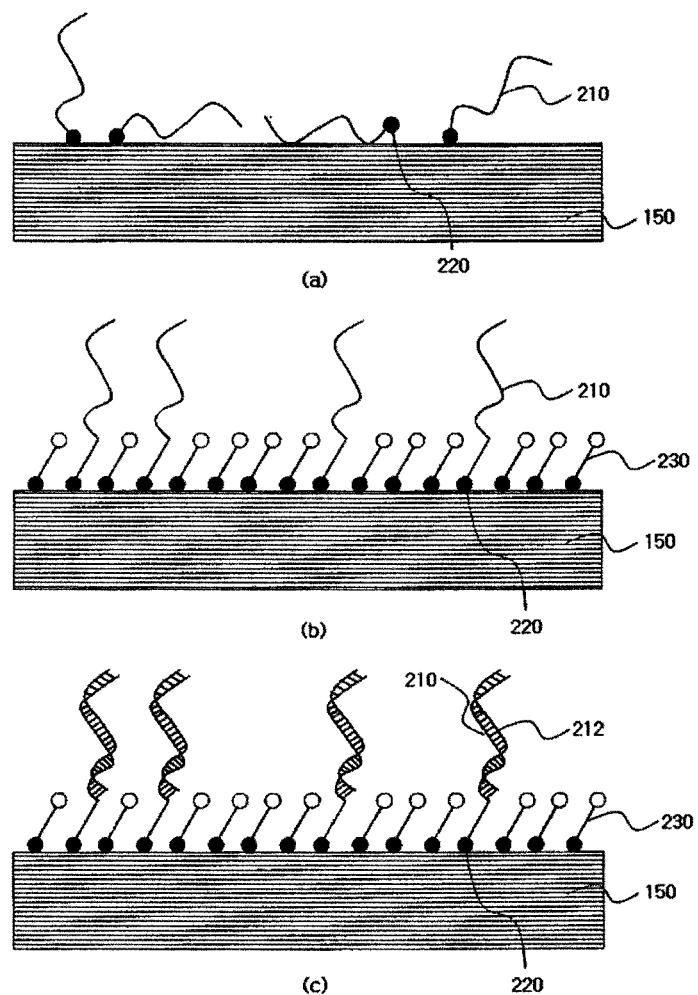
FIG. 5 is a view illustrating processes of sensing biomolecules using the biomolecular sensor shown in FIG. 1.

FIG. 5 illustrates processes of sensing biomolecules using the biomolecular sensor shown in FIG. 1. (a) to (c) of FIG. 5 are respectively, views obtained by enlarging any one of the plurality of metal plates 150 of FIG. 1.

Referring to (a) of FIG. 5, thiolated probe ssDNAs 210 are attached to the metal plate 150 using a combination between a sulfide group (S group) 220 of each of the probe ssDNAs 210 and metal (e.g., gold (Au)) constituting the metal plate 150. The probe ssDNAs 210 are irregularly attached to the metal plate 150 without a directional property. The reason that the thiolated probe ssDNAs are provided is that the thiolated probe ssDNAs are well attached to the metal plate 150.

Referring to (b) of FIG. 5, spacers 230 are attached on the metal plate 150 to which the probe ssDNA 210 are attached. The attached spacers 230 function to arrange the probe ssDNAs 210 to have a directional property, and function to fill between the probe ssDNAs 210 attached to the metal plate 150 so as to secure a space into which biomolecules 212 can enter. Also, the spacer 230 is attached to a metal electrode so as to serve as an insulating layer. For example, mercaptohexanol (MCH) used as the spacer 230 is shown in this figure. The example is illustratively provided, and various other materials may be used as the spacer 230. Alternatively, the spacer may be omitted not to decrease sensitivity of the biomolecular sensor.

Referring to (c) of FIG. 5, a specific biomolecule (e.g., a complementary ssDNA) 212 is combined with each of the probe ssDNAs 210 attached to the metal plate 150. The specific biomolecule 212, i.e., the complementary ssDNA 212 of the probe ssDNA, is selectively combined with the probe ssDNA 210. The combined complementary ssDNAs 212 change electrical properties of the plurality of nanostructures 140 adjacent to the metal plate 150 and change resistance between the first and second electrodes 120 and 130, and the like. Accordingly, the biomolecular sensor senses the specific biomolecules 212.

It is expected that the change in the electrical properties of the plurality of nanostructures 140 results from charges of DNAs attached to the metal plate 150, which comes in contact with the plurality of nanostructures 140. More specifically, the DNA is a polymer of nucleotides, and the nucleotide consists of a 5-carbon sugar, a phosphate group and a nitrogenous base. The phosphate group has a negative (−) charge by the electronegativity difference between oxygen and phosphorus constituting the phosphate group. The metal plate 150 to which the DNAs having the negative (−) charge are attached changes electrical properties of adjacent nanostructures 140. Where the metal plate 150 having the DNAs attached thereto comes in contact with a contact point between the plurality of nanostructures 140 or a contact point between the plurality of nanostructures 140 and the electrodes 120 and 130, ohmic contact and schottky contact properties generated at these contact points are changed. Where the metal plate 150 having the DNAs attached thereto comes in contact with the plurality of nanostructures 140, electrical properties in the plurality of nanostructures 140 are changed, thereby resulting in a change in electrical conductivity of the nanostructures 140. Where the metal plate 150 having the DNAs attached thereto is positioned in a space between the plurality of nanostructures 140, electrical properties in neighboring nanostructures 140 are changed by the electric field of the metal plate 150. The additional combination of the complementary ssDNA causes additional changes in contact properties between the nanostructures 140 and additional changes in electrical properties in the nanostructures 140. Accordingly, the biomolecular sensor senses a specific biomolecule by measuring a change in resistance, and the like.

The illustration is only an embodiment selected for describing operations of the biomolecular sensor. Since aptamers, peptides or antibodies suitable for a specific target molecule are attached on the plurality of metal plates 150, the biomolecular sensor may be used to detect proteins in a solution, tumor markers, molecules, ions, viruses and the like. As another embodiment, the biomolecules to which the plurality of metal plates 150 are exposed may be in a liquid or gaseous phase (or the biomolecules may be included in liquid or gas).

As an embodiment, gold (Au) may be used as a metal for sensing DNAs in the biomolecular sensor having the plurality of metal plates 150. Here, the gold (Au) is deposited to have a thickness of 1 mm through a physical vapor deposition process and then subjected to an annealing process. For example, where the spacer 230 and the probe ssDNA 210 are attached to the metal plate, the molecular sensor can obtain a resistance of 142 KΩ. Where the complementary ssDNA 212 is selectively combined with the probe ssDNA 210, the molecular sensor can obtain a resistance of 1240 KΩ.

$$\text{sensitivity} = \left|\frac{\Delta R}{R_o}\right| \times 100\% \qquad \text{[Equation 1]}$$

In Equation 1, $R_o$ denotes a resistance (hereinafter, referred to as an initial resistance) of the biomolecular sensor, obtained when the spacer 230 and the probe ssDNA 210 are attached, and $\Delta R$ denotes a difference between the initial resistance $R_o$ and a resistance obtained when the complementary ssDNA 212 is additionally combined.

When the sensitivity is defined as shown in Equation 1, a sensitivity of about 773% can be obtained in the above embodiment. Meanwhile, according to "B. L. Allen, P. D. Kichambare, A. Star, "Carbon Nanotube Field-Effect-Transistor-Based Biosensors," Adv. Mater. Vol. 19, pp. 1439-1451, 2007," a sensitivity of about 16.3% can be obtained. Consequently, the sensitivity of the biomolecular sensor having the plurality of metal plates 150 according to the embodiment of present invention can be increased over 47 times greater than that of the conventional biomolecular sensor. Thus, it can be seen that the sensitivity of the biomolecular sensor is remarkably improved by attaching the plurality of metal plates 150.

In the embodiment, a method of sensing biomolecules through a change in current measured by applying a voltage between the first and second electrodes 120 and 130 is used as the method of detecting the biomolecules. However, some biomolecules can be sensed using a method of measuring channel characteristics of biomolecules attached to the plurality of metal plates 150 by configuring field effect transistors (FETs). In each of the FETs, the substrate 110, the first electrode 120, the second electrode 130 and the plurality of nanostructures 140 may be used as a gate electrode, a source electrode, a drain electrode and a channel, respectively. The aforementioned example is illustratively provided, and the biomolecules may be sensed using various other methods of measuring a change in the electrical properties of the plurality of nanostructures 140.

FIGS. 6 to 10 illustrate processes in a method of fabricating the biomolecular sensor according to the first embodiment of the present invention. (a) and (b) of each of the figures show plan and sectional views of the biomolecular sensor, respectively. The sectional view in each of the figures is a sectional view taken along line E-E' of the plan view. A method of fabricating the biomolecular sensor according to the first and second modifications in the first embodiment of the present invention, a method of fabricating the biomolecular sensor according to the second embodiment of the present invention and a method of fabricating the biomolecular sensor according to the third embodiment of the present invention can be derived with reference to the method of fabricating the biomolecular sensor according to the first embodiment of the present invention.

Referring to FIG. 6, a substrate 110 is first prepared. Although various substrates may be used as the substrate 110 as described above, an example in which a semiconductor substrate is used as the substrate 110 is shown in this figure.

Referring to FIG. 7, an insulating layer 160 is formed on the substrate 110. The process of forming the insulating layer 160 is well known in the art, and thus, its detailed description will be omitted for convenience of illustration.

Figure 8:
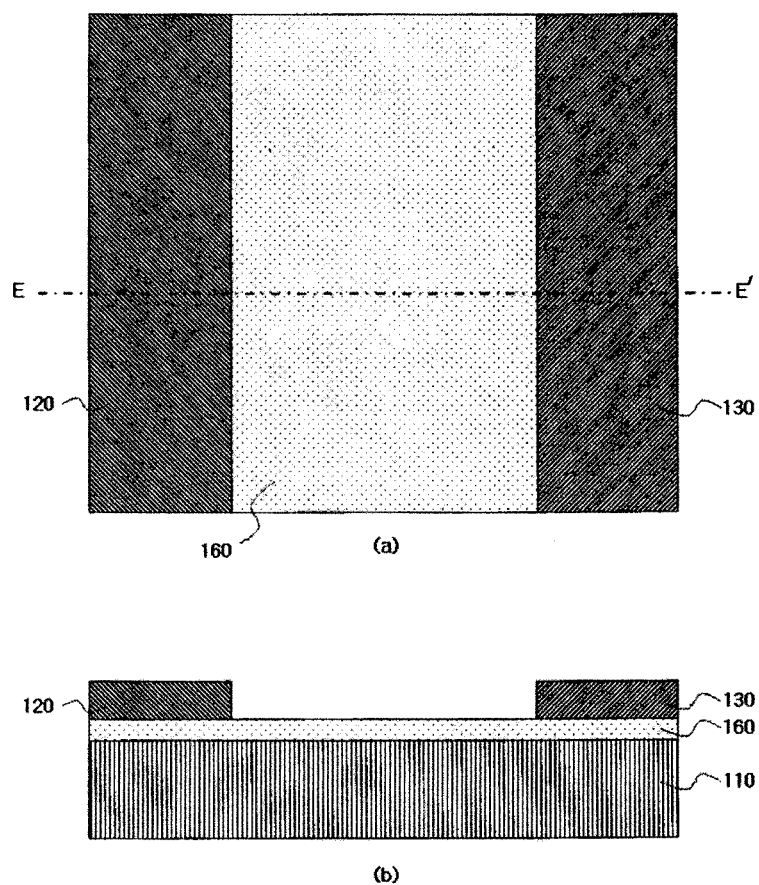

Referring to FIG. 8, first and second electrodes 120 and 130 electrically isolated from each other are formed on the insulating layer 160. As described above, various materials may be used as the first and second electrodes 120 and 130. The process of forming the electrodes is well known in the art, and thus, its detailed description will be omitted for convenience of illustration.

Figure 9:
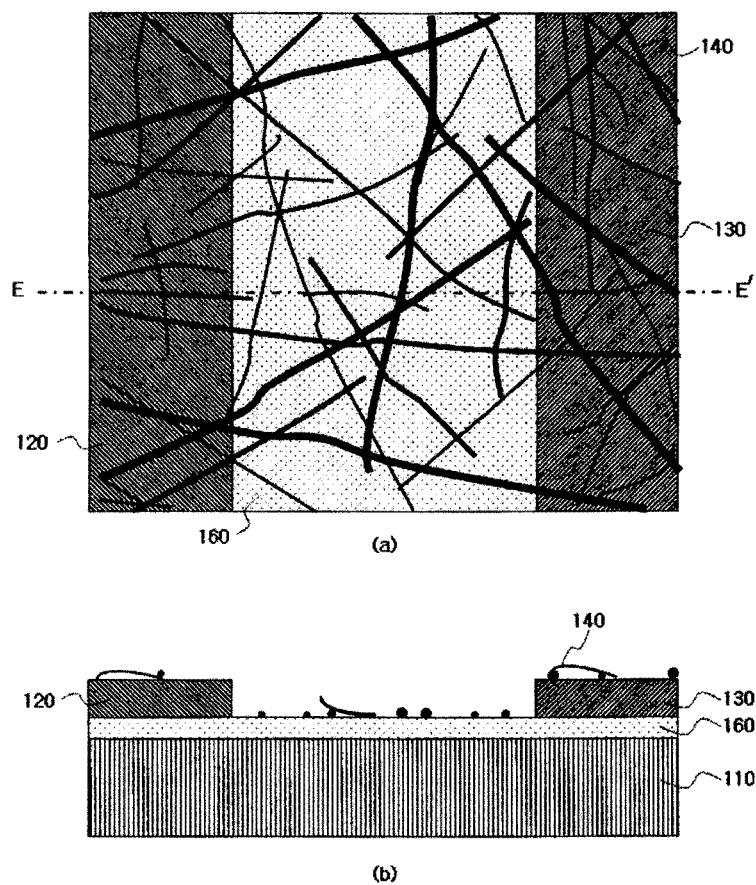
Figure 10:
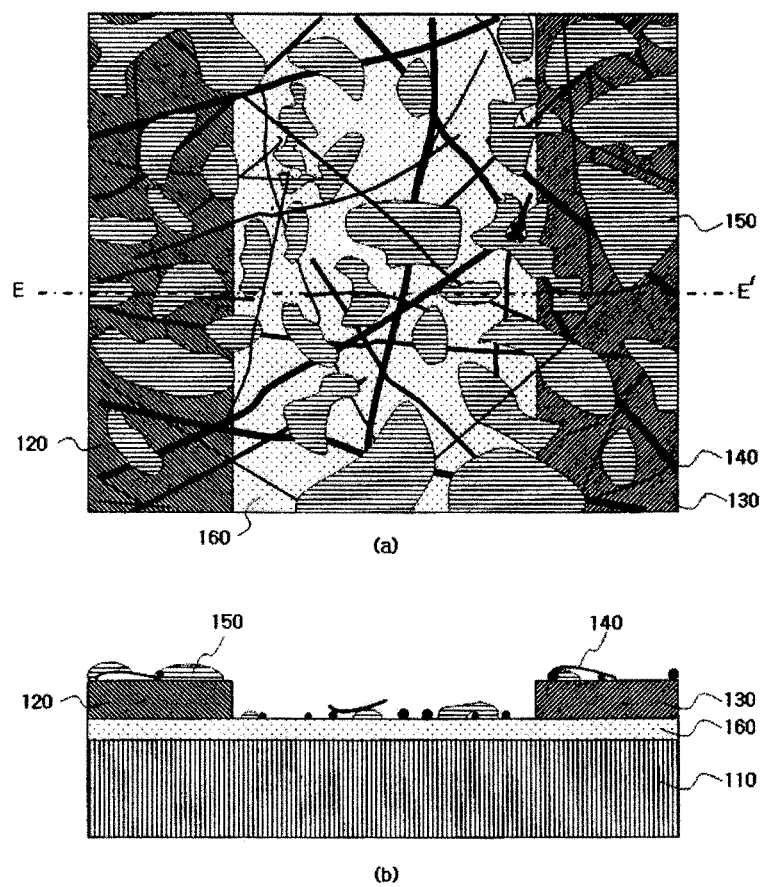

Referring to FIG. 9, a plurality of nanostructures 140 are formed on the first and second electrodes 120 and 130 and the insulating layer 160. The plurality of nanostructures 140 connect the first and second electrodes 120 and 130 to each other. The combination relation of the plurality of nanostructures that connect the first and second electrodes 120 and 130 can be easily derived with reference to the first embodiment, and thus, its description will be omitted for convenience of illustration.

As an embodiment, the plurality of nanostructures 140 may be formed by a process of immersing the substrate 110 in a solution having the nanostructures (e.g., CNTs) 140 dispersed therein, and a process of extracting the substrate 110 from the solution. For example, the solution having the CNTs dispersed therein may be obtained by mixing the CNTs and 1.2-dichlorobenzene at a ratio of 0.02 g to 200 ml. The immersion of the substrate 110 may be performed, for example, for 1 to 5 minutes, and the extraction speed of the substrate 110 may be, for example, 1 to 10 mm/min Referring to FIG. 10, a plurality of metal plates 150 are formed on the plurality of nanostructures 140. The plurality of metal plates 150 are formed by depositing a metal through a physical vapor deposition process and then performing an annealing process. In some embodiment, the annealing process may not be performed. The physical vapor deposition process is a method of directly depositing a metal on surfaces of the plurality of nanostructures 140, and can minimize surface damage of the plurality of nanostructures 140. The size of metal particles can be easily adjusted by controlling deposition conditions such as temperature, pressure and time. Also, a series of processes can be performed by using a semiconductor process, and thus productivity can be improved. For example, thermal evaporation may be used as the physical vapor deposition process, and the annealing process may be performed under a temperature of about 400° C. and a pressure of about $10^{-6}$ torr for about 30 minutes. The example is illustratively provided, and conditions of the physical vapor deposition process and the annealing process may be variously modified. For example, the physical vapor deposition process may include sputtering, pulsed laser deposition (PLD), atomic layer deposition (ALD) and the like, and the temperature, pressure and time may be varied as conditions of the annealing process.

Although the present invention has been explained by the embodiments shown in the drawings described above, it should be understood to the ordinary skilled person in the art that the present invention is not limited to the embodiments but rather that various changes or modifications thereof are possible without departing from the spirit of the present invention. Accordingly, the scope of the present invention shall be determined only by the appended claims and their equivalents.

The invention claimed is:

1. A biomolecular sensor comprising:
   a substrate;
   first and second electrodes disposed to be spaced apart from each other on the substrate;
   a plurality of nanostructures disposed on the substrate and configured to connect the first and second electrodes to each other, the first and second electrodes being disposed on at least one of the plurality of nanostructures,
   wherein at least one of said nanostructures is electrically connected to another one of said nanostructures and/or connected to said plurality of nanostructures as an entangled mesh; and
   a plurality of metal plates configured to change electrical properties of the plurality of nanostructures according to the attachment of biomolecules,
   wherein at least one of the plurality of metal plates is positioned to come in contact with a top or bottom side of the plurality of nanostructures.

2. The biomolecular sensor of claim 1, wherein the plurality of nanostructures comprise carbon nanotubes.

3. The biomolecular sensor of claim 1, wherein the plurality of metal plates comprise gold (Au).

4. The biomolecular sensor of claim 1, further comprising thiolated probe ssDNAs attached to the plurality of metal plates and selectively combined with the biomolecules.

5. The biomolecular sensor of claim 1, further comprising an insulating layer disposed on the substrate and positioned below the first and second electrodes, the plurality of nanostructures and the plurality of metal plates.

6. The biomolecular sensor of claim 1, wherein the biomolecules are attached to the plurality of metal plates and have charges, and the charges change electrical properties in the plurality of nanostructures through the plurality of metal plates.

7. The biomolecular sensor of claim 1, wherein the biomolecules are attached to the plurality of metal plates and have charges, and the charges change electrical properties in contact points through the plurality of metal plates, wherein each of the contact points is a portion at which one of the plurality of nanostructures is connected to another of the plurality of nanostructures.

8. The biomolecular sensor of claim 1, wherein the plurality of metal plates have a planar structure in which an area of a top surface of the plurality of metal plates has a size greater than that of a square of a thickness of the plurality of metal plates.

9. The biomolecular sensor of claim 1, wherein the plurality of metal plates have a planar structure in which an area of a top surface of the plurality of metal plates has a size four times greater than that of a square of a thickness of the plurality of metal plates.

10. The biomolecular sensor of claim 1, wherein the second electrode surrounds the first electrode.

11. The biomolecular sensor of claim 10, wherein a reference voltage that is a predetermined voltage is applied to the second electrode.

12. A biomolecular sensor comprising:
    a substrate;
    first and second electrodes disposed to be spaced apart from each other on the substrate;
    a plurality of nanostructures disposed on the substrate and configured to connect the first and second electrodes to each other, the first and second electrodes being disposed on said plurality of nanostructures, wherein at least one of said nanostructures is electrically connected to another one of said nanostructures and/or connected to said plurality of nanostructures as an entangled mesh;
    a plurality of metal plates configured to change electrical properties of the plurality of nanostructures according to the attachment of biomolecules, wherein at least one of the plurality of metal plates is positioned to come in contact with a top or bottom side of the plurality of nanostructures; and
    thiolated probe ssDNAs attached to the plurality of metal plates and selectively combined with the biomolecules, wherein a spacer connects between at least one of said metal plates and one of said thiolated probe ssDNAs.

* * * * *